US011285048B2

(12) United States Patent
Locke

(10) Patent No.: US 11,285,048 B2
(45) Date of Patent: Mar. 29, 2022

(54) MULTI-LAYER COMPARTMENT DRESSING AND NEGATIVE-PRESSURE TREATMENT METHOD

(71) Applicant: KCI Licensing, Inc., San Antonio, TX (US)

(72) Inventor: Christopher Brian Locke, Bournemouth (GB)

(73) Assignee: KCI Licensing, Inc., San Antonio, TX (US)

( * ) Notice: Subject to any disclaimer, the term of this patent is extended or adjusted under 35 U.S.C. 154(b) by 24 days.

(21) Appl. No.: 16/632,651

(22) PCT Filed: Jul. 24, 2018

(86) PCT No.: PCT/US2018/043444
§ 371 (c)(1),
(2) Date: Jan. 21, 2020

(87) PCT Pub. No.: WO2019/027731
PCT Pub. Date: Feb. 7, 2019

(65) Prior Publication Data
US 2020/0170842 A1    Jun. 4, 2020

Related U.S. Application Data

(60) Provisional application No. 62/540,404, filed on Aug. 2, 2017.

(51) Int. Cl.
*A61F 13/00* (2006.01)
*A61F 13/02* (2006.01)
*A61M 1/00* (2006.01)

(52) U.S. Cl.
CPC .... *A61F 13/00068* (2013.01); *A61F 13/0289* (2013.01); *A61M 1/90* (2021.05);
(Continued)

(58) Field of Classification Search
CPC ............ A61F 13/00068; A61F 13/0289; A61F 2013/00604; A61F 2013/00676; A61M 1/0088
See application file for complete search history.

(56) References Cited

U.S. PATENT DOCUMENTS 1,355,846 A    10/1920    Rannells
2,547,758 A    4/1951    Keeling
(Continued)

FOREIGN PATENT DOCUMENTS

AU    550575 B2    3/1986
AU    745271 B2    3/2002
(Continued)

OTHER PUBLICATIONS

Louis C. Argenta, MD and Michael J. Morykwas, PhD; Vacuum-Assisted Closure: A New Method for Wound Control and Treatment Clinical Experience; Annals of Plastic Surgery; vol. 38, No. 6, Jun. 1997; pp. 563-576.
(Continued)

*Primary Examiner* — Andrew J Mensh
*Assistant Examiner* — Nhu Q. Tran

(57) ABSTRACT

A dressing for treating a tissue site, particularly a peritoneal or abdominal site, is disclosed. The dressing may comprise: first and second layers, each being made from a liquid-impermeable material and being at least partially fenestrated, the layers being coupled together to define a chamber therebetween; and disposed within the chamber a third layer comprising a manifold having a central region, and a perimeter region containing perforations arranged in a pattern defining a plurality of sub-regions. The first and second layers can be coupled using a plurality of welds or bonds through the perimeter region perforations. Optionally, the manifold does not comprise, and the chamber does not contain, any manifolding elements extending outward from an outer edge of the perimeter region.

14 Claims, 5 Drawing Sheets

(52) U.S. Cl.
CPC ........... *A61F 2013/00604* (2013.01); *A61F 2013/00676* (2013.01); *A61M 2205/3324* (2013.01); *A61M 2205/3344* (2013.01); *A61M 2205/3368* (2013.01); *A61M 2205/3592* (2013.01); *A61M 2210/1017* (2013.01); *A61M 2210/1021* (2013.01)

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,730,737 B1* | 5/2004 | De Keyzer ............ C08L 91/00 525/105 |
| 6,814,079 B2 | 11/2004 | Heaton et al. |
| 7,846,141 B2 | 12/2010 | Weston |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,398,614 B2 | 3/2013 | Blott et al. |
| 8,449,509 B2 | 5/2013 | Weston |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,679,081 B2 | 3/2014 | Heagle et al. |
| 8,834,451 B2 | 9/2014 | Blott et al. |
| 8,926,592 B2 | 1/2015 | Blott et al. |
| 9,017,302 B2 | 4/2015 | Vitaris et al. |
| 9,198,801 B2 | 12/2015 | Weston |
| 9,211,365 B2 | 12/2015 | Weston |
| 9,289,542 B2 | 3/2016 | Blott et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2004/0030304 A1* | 2/2004 | Hunt ................ A61F 13/00042 604/317 |
| 2009/0287133 A1* | 11/2009 | LaGreca, Sr. ....... A61F 13/0213 602/54 |
| 2011/0224630 A1 | 9/2011 | Simmons et al. |
| 2011/0224631 A1* | 9/2011 | Simmons .......... A61F 13/00995 604/319 |
| 2012/0010578 A1* | 1/2012 | Hirsch ................ A61M 1/0058 604/290 |
| 2014/0163491 A1 | 6/2014 | Schuessler et al. |
| 2014/0316353 A1 | 10/2014 | Riesinger |
| 2015/0080788 A1 | 3/2015 | Blott et al. |
| 2017/0182230 A1* | 6/2017 | Ingram .................. A21B 3/18 |
| 2017/0209641 A1* | 7/2017 | Mercer ............... A61M 1/0088 |

FOREIGN PATENT DOCUMENTS

| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |

(56) References Cited

FOREIGN PATENT DOCUMENTS

| | | |
|---|---|---|
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2195255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/20041 A1 | 9/1994 |
| WO | 96/05873 A1 | 2/1996 |
| WO | 97/18007 A1 | 5/1997 |
| WO | 99/13793 A1 | 3/1999 |
| WO | 2016015001 A2 | 1/2016 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & Apr. 29, 1997.

PCT Written Opinion, PCT International Application PCT/GB96/02802; dated Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96.

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinoví?, V. ?uki?, Ž. Maksimoví?, ?. Radak, and P. Peška, "Vacuum Therapy in the Treatment of Peripheral Blood Vessels," Timok Medical Journal 11 (1986), pp. 161-164.

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

(56) References Cited

OTHER PUBLICATIONS

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians; Jul. 2007.

* cited by examiner

MULTI-LAYER COMPARTMENT DRESSING AND NEGATIVE-PRESSURE TREATMENT METHOD

TECHNICAL FIELD

The invention set forth in the appended claims relates generally to tissue treatment systems and more particularly, but without limitation, to abdominal treatment systems with negative pressure and optionally instillation.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," "vacuum-assisted closure," and "topical negative-pressure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

There is also widespread acceptance that cleansing a tissue site can be highly beneficial for new tissue growth. For example, a wound can be washed out with a stream of liquid solution, or a cavity can be washed out using a liquid solution for therapeutic purposes. These practices are commonly referred to as "irrigation" and "lavage" respectively. "Instillation" is another practice that generally refers to a process of slowly introducing fluid to a tissue site and leaving the fluid for a prescribed period of time before removing the fluid. For example, instillation of topical treatment solutions over a tissue site can be combined with negative-pressure therapy to further promote tissue healing by loosening soluble contaminants at a tissue site and removing infectious material. As a result, soluble bacterial burden can be decreased, contaminants removed, and the tissue site cleansed.

While the clinical benefits of negative-pressure therapy and/or instillation therapy are widely known, improvements to therapy systems, components, and processes may benefit healthcare providers and patients.

BRIEF SUMMARY

New and useful systems, apparatuses, and methods for treating a tissue site in a negative-pressure therapy environment are set forth in the following summary and description, as well as in the appended claims. Illustrative embodiments are also provided to enable a person skilled in the art to make and use the claimed subject matter.

For example, a dressing for treating a tissue site may comprise a sheet of reticulated foam between two fenestrated film layers. In some embodiments, the film layers may be polyurethane drape layers. The dressing can have a variety of shapes, such as substantially oval or hexagonal. The film layers may be welded or bonded together, and may encapsulate the foam in some examples. For example, the film layers may be bonded with RF welding, ultrasonic welding, adhesives, or some combination. The bonding can be registered or aligned with voids or perforations in the foam, or the film layers may be bonded through the foam in some embodiments. The bonds may be spaced so that they do not inhibit fluid flow through the foam or the ability to size the dressing, and close enough to maintain the structural integrity of the dressing a single unit.

More generally, in some embodiments, a dressing for treating a tissue site may include a first layer and a second layer coupled to each other to define a chamber therebetween, and a third layer disposed within the chamber. Each of the first and second layers may individually be made from a liquid-impermeable material and may be at least partially fenestrated. In some embodiments, the third layer may comprise a manifold having a central region and a perimeter region, with the perimeter region containing perforations arranged in a pattern that defines a plurality of sub-regions. In more particular examples, the first and second layers may be coupled together by a plurality of welds or bonds through at least some of the perforations in the perimeter region of the third layer comprising the manifold. In some example embodiments, the chamber may comprise a plurality of fluid removal pathways, substantially all of which may be through the manifold.

Alternatively, in other example embodiments, a system for treating a tissue site may include a dressing comprising a manifold layer and a plurality of fluid pathways therethrough, as well as a negative-pressure source fluidly coupled to the plurality of fluid removal pathways via the manifold layer. The dressing may be configured for deploying in a compartmented tissue site, such as in an abdominal cavity. In some embodiments, the system may further include a fluid source coupled to and in fluid communication with the dressing and a plurality of fluid delivery pathways formed within the chamber and configured to be in fluid communication with the fluid source. In some such embodiments, the fluid delivery pathways may also be in fluid communication with the fluid removal pathways via the manifold layer.

Alternatively, in other example embodiments, a method for treating a compartmented wound site, such as a peritoneal or abdominal cavity, may include: opening the compartmented wound site to form an open cavity; deploying within the compartmented wound site a dressing or at least a portion of a system for treating a tissue site; and deploying a cover to form a fluid seal over the open cavity. In some embodiments, the method may additionally include deploying a negative-pressure connector subsystem; fluidly coupling the negative-pressure connector subsystem to a negative-pressure source; and activating the negative-pressure source.

Objectives, advantages, and a preferred mode of making and using the claimed subject matter may be understood best by reference to the accompanying drawings in conjunction with the following detailed description of illustrative embodiments.

DESCRIPTION OF EXAMPLE EMBODIMENTS

The following description of example embodiments provides information that enables a person skilled in the art to make and use the subject matter set forth in the appended claims, but may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

Figure 1:
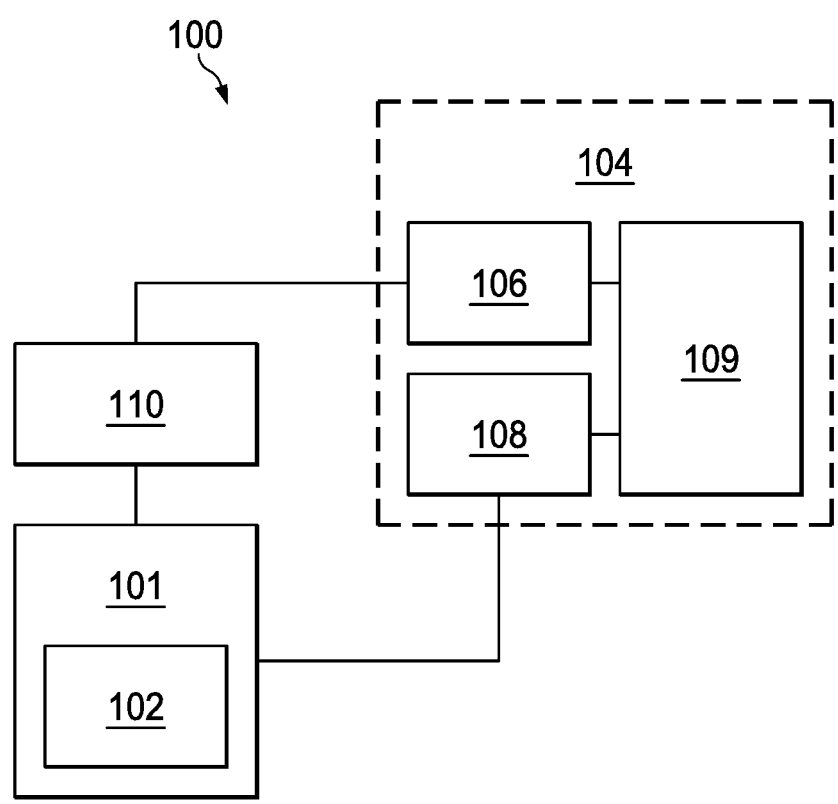
FIG. 1 is a functional block diagram of an example embodiment of a therapy system that can deliver negative pressure as well as a treatment fluid to a tissue site and can manage fluids in accordance with this specification.

FIG. 1 is a simplified functional block diagram of an example embodiment of a therapy system 100 that can provide negative-pressure therapy, optionally along with instillation of topical treatment solutions, to a tissue site in accordance with this specification.

The term "tissue site" in this context broadly refers to a wound, defect, or other treatment target located on or within tissue, particularly compartmented tissue, including but not limited to, bone tissue, adipose tissue, muscle tissue, neural tissue, dermal tissue, vascular tissue, connective tissue, cartilage, tendons, or ligaments. Compartmented tissue may include a wound, defect, or other treatment target in a body cavity, such as an abdominal cavity, for example.

The therapy system 100 may include a therapy unit 104 and a treatment device 101 including a dressing 102. In some embodiments, the therapy unit 104 may include a negative-pressure source, such as negative-pressure source 106, optionally a fluid source, such as fluid source 108, and a regulator or controller 109. In other embodiments, the therapy unit 104 may include the negative-pressure source 106, while the optional fluid source 108 and/or the controller 109 may be freestanding, separate units. The therapy system 100 may optionally also include additional components, such as a container 110, which may be coupled to or in fluid communication with at least the treatment device 101, the dressing 102, the therapy unit 104, and the negative pressure source 106, whether directly or indirectly.

Components of the therapy system 100 may be fluidly coupled to each other to provide a path for transferring fluids (i.e., liquid and/or gas) between the components. For example, components may be fluidly coupled through a fluid conductor, such as a tube. A "tube," as used herein, broadly includes a tube, pipe, hose, conduit, or other structure with one or more lumina adapted to convey a fluid between two ends. Typically, a tube is an elongated, cylindrical structure with some flexibility, but the geometry and rigidity may vary. In some embodiments, components may also be coupled by virtue of physical proximity, being integral to a single structure, or being formed from the same piece of material. Moreover, some fluid conductors may be molded into or otherwise integrally combined with other components. Coupling may also include mechanical, thermal, electrical, or chemical coupling (such as a chemical bond) in some contexts. For example, a tube may mechanically and fluidly couple the treatment device 101 to the therapy unit 104 in some embodiments. In general, components of the therapy system 100 may be coupled directly or indirectly.

The negative-pressure source 106 may be configured to be coupled to a distribution component, such as the dressing 102, for example. In general, a distribution component may refer to any complementary or ancillary component configured to be fluidly coupled to a negative-pressure supply in a fluid path between a negative-pressure supply and a tissue site. A distribution component is preferably detachable, and may be disposable, reusable, or recyclable. For example, the dressing 102 of the treatment device 101 may be fluidly coupled to the negative-pressure source 106 of the therapy unit 104, as illustrated in FIG. 1. In some embodiments, the treatment device 101 may include the dressing 102, as well as additional tissue interfaces, fluid conduits, and/or a cover. In some embodiments, a dressing interface may facilitate coupling the negative-pressure source 106 to the dressing 102 of the treatment device 101. For example, such a dressing interface may be a T.R.A.C.® Pad, Sensa-T.R.A.C.® Pad, or VeraT.R.A.C™ Pad, or VeraT.R.A.C™ Duo Tubing Set available from KCI of San Antonio, Tex.

The fluid mechanics of using a negative-pressure source to reduce pressure in another component or location, such as within a sealed therapeutic environment, can be mathematically complex. However, the basic principles of fluid mechanics applicable to negative-pressure therapy and instillation are generally well-known to those skilled in the art, and the process of reducing pressure may be described illustratively herein as "delivering," "distributing," or "generating" negative pressure, for example.

In general, exudates and other fluids flow toward lower pressure along a fluid path. Thus, the term "downstream" typically implies something in a fluid path relatively closer to a source of negative pressure or further away from a source of positive pressure. Conversely, the term "upstream" implies something relatively further away from a source of negative pressure or closer to a source of positive pressure. Similarly, it may be convenient to describe certain features in terms of fluid "inlet" or "outlet" in such a frame of reference. This orientation is generally presumed for purposes of describing various features and components herein. However, the fluid path may also be reversed in some applications (such as by substituting a positive-pressure source for a negative-pressure source) and this descriptive convention should not be construed as a limiting convention.

"Negative pressure" generally refers to a pressure less than a local ambient pressure, such as the ambient pressure in a local environment external to a sealed therapeutic environment provided by the treatment device 101 or the dressing 102. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. Similarly, references to increases in negative pressure typically refer to a decrease in absolute pressure, while decreases in negative pressure typically refer to an increase in absolute pressure. While the amount and nature of negative pressure applied to a tissue site may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −50 mm Hg (−6.7 kPa) and −300 mm Hg (−39.9 kPa).

A negative-pressure supply, such as the negative-pressure source 106 of the therapy unit 104, may be a reservoir of air at a negative pressure, or may be a manual or electrically-powered device that can reduce the pressure in a sealed volume, such as a vacuum pump, a suction pump, a wall suction port available at many healthcare facilities, or a micro-pump, for example. A negative-pressure supply may be housed within or used in conjunction with other components, such as sensors, processing units, alarm indicators, memory, databases, software, display devices, or user interfaces that further facilitate therapy, such as through the use of therapy unit 104. A negative-pressure supply may also have one or more supply ports configured to facilitate coupling and de-coupling the negative-pressure supply to one or more distribution components.

In some embodiments, the therapy system 100 may include one or more sensors, such as a pressure sensor, an electric sensor, a temperature sensor, a pH sensor, a relative humidity sensor, or a combination thereof, to measure one or more operating parameters and provide feedback signals to the controller 109 indicative of the operating parameters. In some embodiments if present, the pressure sensor may also be coupled, or configured to be coupled, to a distribution component and to the negative-pressure source 106, which may, for example, include wireless connection. Additionally or alternatively, a sensor may be configured to provide information to a person, who can then manually control one or more operating parameters externally. Sensors, such as pressure sensors or electric sensors, are generally known in the art as any apparatus operable to detect or measure a physical phenomenon or property, and generally provide a signal indicative of the phenomenon or property that is detected or measured. If present, a pressure sensor may be a transducer configured to measure pressure in a pneumatic pathway and convert the measurement to a signal indicative of the pressure measured, in some embodiments. If present, for example, a pressure sensor may be a piezoresistive strain gauge in some embodiments. If present, an electric sensor may optionally measure operating parameters of the negative-pressure source 106, such as voltage or current, in some embodiments. Also if present, the signals from a pressure sensor and an electric sensor may be suitable as an input signal to the controller 109, but some signal conditioning may be appropriate in some embodiments. For example, in such embodiments the signal may need to be filtered or amplified before it can be processed by the controller 109. Typically in such embodiments, the signal is an electrical signal, but may be represented in other forms, such as an optical signal. If a sensor is meant to monitor conditions at or near a tissue site or sealed volume, then it may be advantageous for the sensor to be placed as close as practical or possible to the site(s) desired to be monitored. In various embodiments, if present, a pressure sensor may be placed in a conduit in fluid communication with the negative-pressure source 106 but proximate to the sealed volume, for example near, on, or in one or more layers of the dressing 102.

In some embodiments, the dressing 102 may comprise a manifold. A "manifold" in this context generally includes any substance or structure providing a plurality of pathways adapted to collect or distribute fluid across a tissue site under pressure. For example, a manifold may be adapted to receive negative pressure from a source and distribute negative pressure through multiple apertures across a tissue site, which may have the effect of collecting fluid from across a tissue site and drawing the fluid toward the source. In some embodiments, the fluid path may be reversed or a secondary fluid path may be provided to facilitate delivering fluid across a tissue site.

In some illustrative embodiments, the pathways of a manifold may be interconnected to improve distribution or collection of fluids across a tissue site. In some illustrative embodiments, a manifold may be a porous foam material having interconnected cells or pores. For example, cellular foam, open-cell foam, reticulated foam, porous tissue collections, and other porous material such as gauze or felted mat generally include pores, edges, and/or walls adapted to form interconnected fluid channels. Liquids, gels, and other foams may also include or be cured to include apertures and fluid pathways. In some embodiments, a manifold may additionally or alternatively comprise projections that form interconnected fluid pathways. For example, a manifold may be molded to provide surface projections that define interconnected fluid pathways.

The average pore size of a foam may vary according to needs of a prescribed therapy. For example, in some embodiments, the manifold may be a foam having pore sizes in a range of 400-600 microns. The tensile strength of the manifold may also vary according to needs of a prescribed therapy. For example, the tensile strength of a foam may be increased for instillation of topical treatment solutions. In some embodiments, a manifolding member may include a polyurethane foam which may be between 6 mm and 10 mm in thickness. In some embodiments, a manifolding member may include a felted foam which may be between 1 mm and 3 mm in thickness. In one non-limiting example, the manifold may comprise or be an open-cell, reticulated polyurethane foam such as GRANUFOAM™ Dressing or VERA-FLO™ Therapy foam, both available from KCI Licensing, Inc. of San Antonio, Tex. Other non-limiting examples of manifolds can include Libeltex TDL2, Libeltex TL4, Baltex 3DXD spacer fabrics, Baltex 4DXD spacer fabrics, embossed films, or some other formed structure. Some embodiments may include a manifolding member having additional layers or materials, such as absorptive materials, wicking materials, hydrophobic materials, and hydrophilic materials.

A manifold may be either hydrophobic or hydrophilic. In an example in which the manifold may be hydrophilic, the manifold may also wick fluid away from a tissue site, while continuing to distribute negative pressure to the tissue site. The wicking properties of the manifold may draw fluid away from a tissue site by capillary flow or other wicking mechanisms. An example of a hydrophilic foam is a polyvinyl alcohol, open-cell foam such as V.A.C. WHITEFOAM™ dressing available from KCI Licensing, Inc. of San Antonio, Tex. Other hydrophilic foams may include those made from polyether. Other foams that may exhibit hydrophilic characteristics include hydrophobic foams that have been treated or coated to provide hydrophilicity.

Manifold materials may further promote granulation at a tissue site when pressure within the sealed therapeutic environment is reduced. For example, any or all of the surfaces of the portions of the dressing 102, including the manifold, may have an uneven, coarse, or jagged profile that can induce microstrains and stresses at a tissue site if negative pressure is applied across the manifold, or across the dressing 102 generally.

In operation, the dressing 102 can often include a tissue interface that may be placed within, over, on, or otherwise proximate to a tissue site. A cover may be placed over a tissue interface and sealed to an attachment surface near the tissue site. For example, a cover may be sealed to undamaged epidermis peripheral to a tissue site. Thus, the dressing 102 can provide a sealed therapeutic environment proximate to a tissue site, substantially isolated from the external environment, and the negative-pressure source 106 can reduce the pressure in the sealed therapeutic environment. Negative pressure applied across the tissue site through a tissue interface in the sealed therapeutic environment can induce macrostrain and microstrain in the tissue site, as well as remove exudates and other fluids from the tissue site, which can be collected in a container such as container 110.

In some embodiments, a tissue interface may be constructed from biodegradable materials. Suitable biodegradable materials may include, without limitation, a polymeric blend of polylactic acid (PLA) and polyglycolic acid (PGA). The polymeric blend may also include without limitation polycarbonates, polyfumarates, and capralactones. A tissue interface may further serve as a scaffold for new cell-growth, or a scaffold material may be used in conjunction with the tissue interface to promote cell-growth. A scaffold is generally a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxyapatites, carbonates, or processed allograft materials.

The therapy system 100 may optionally also include a source of instillation fluid or solution. For example, a fluid source 108 may be fluidly coupled to the treatment device 101, and thus the dressing 102, as illustrated in the example embodiment of FIG. 1. The fluid source 108 may be fluidly coupled to a positive-pressure source in some embodiments, or may be fluidly coupled to the negative-pressure source 106. A regulator, such as an instillation regulator, may also be fluidly coupled to the fluid source 106 and the treatment device 101. In some embodiments, an instillation regulator may be fluidly coupled to the negative-pressure source 106 through the treatment device 101, and thus through the dressing 102.

A fluid source, such as the fluid source 108, may be housed within or used in conjunction with other components to facilitate movement of a fluid. The fluid source 108 may be a fluid pump, for example a peristaltic pump. Alternatively, in some embodiments, the fluid source 108 may be a fluid reservoir, which may store and deliver fluid. In any embodiment, the fluid source 108, such as a fluid pump or a fluid reservoir, may include the container 110 repurposed from collecting exudates and other fluids during application of negative pressure, which container can be a canister, pouch, or other storage component.

The fluid source 108 may also be representative of a container, canister, pouch, bag, or other storage component, which can be used to manage exudates and other fluids withdrawn from a tissue site, can provide a solution for instillation therapy, or both. Compositions of solutions may vary according to a prescribed therapy, but examples of solutions that may be suitable for some prescriptions include hypochlorite-based solutions, silver nitrate (0.5%), sulfur-based solutions, biguanides, cationic solutions, saline solutions, and isotonic solutions. In many environments, a rigid container may be preferred or required for collecting, storing, and disposing of fluids. In other environments, fluids may be properly disposed of without rigid container storage, and a re-usable container could reduce waste and costs associated with negative-pressure therapy.

A controller, such as the controller 109, may be a microprocessor or computer programmed to operate one or more components of the therapy system 100, such as the negative-pressure source 106 and the fluid source 108. In some embodiments, for example, the controller 109 may be a microcontroller, which generally comprises an integrated circuit containing a processor core and a memory programmed to directly or indirectly control one or more operating parameters of the therapy system 100. Operating parameters may include the power applied to the negative-pressure source 106, the pressure generated by the negative-pressure source 106, or the pressure distributed to the treatment device 101, for example. Additional operating parameters may include the power applied to the fluid source 108, flow rate of instillation fluid provided by the fluid source 108, or volume of fluid distributed to the treatment device 101. The controller 109 is also preferably configured to receive one or more input signals, such as a feedback signal, and programmed to modify one or more operating parameters based on the input signals.

In some embodiments, the negative-pressure source 106, fluid source 108, controller 109, and container 110 may be integrated within a single therapy unit, such as therapy unit 104. For example, the therapy system 100 may therefore include the treatment device 101 along with a therapy unit 104 such as a V.A.C.ULTA™ therapy unit, V.A.C.IN-STILL™ wound therapy system, INFOV.A.C.™ therapy unit, each available from KCI Licensing, Inc. of San Antonio, Tex., or other suitable therapy units or systems. For example, in some embodiments, the therapy unit 104 may comprise or consist essentially of a V.A.C.ULTA™ unit, which may include software modules specific to negative-pressure therapy in combination with fluid instillation therapy, and specific for use with abdominal dressing systems, such as embodiments of the treatment device 101. Alternatively, any other device capable of providing negative-pressure therapy may be suitable along with any mechanical fluid instillation device, or any negative-pressure therapy device in combination with a manually-managed fluid instillation source, such as a gravity-fed fluid vessel, manual fluid pump, or monitored IV bag or bottle.

Figure 2:
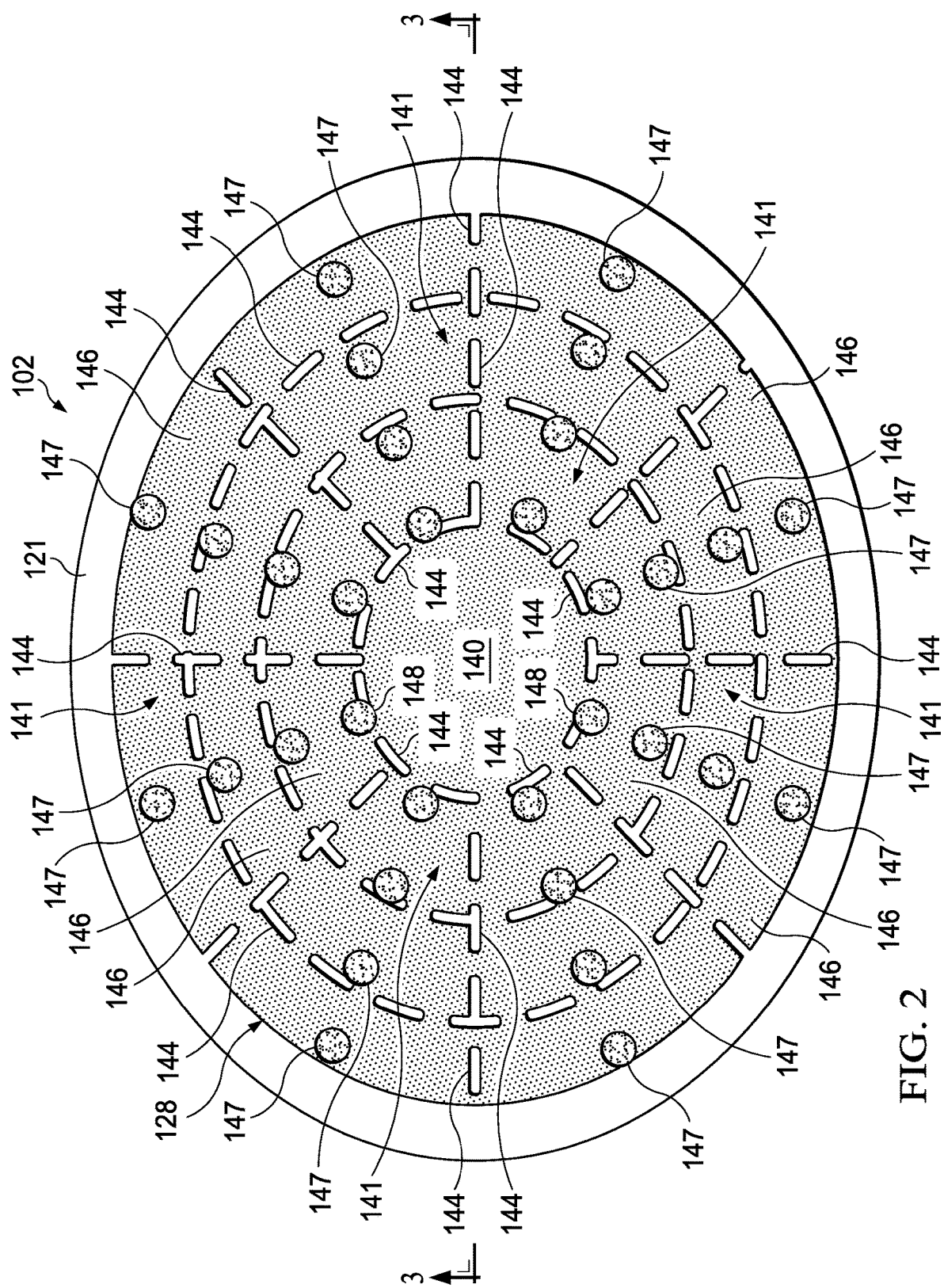
FIG. 2 is a schematic diagram, from a top view, of an example of a dressing that may be associated with some embodiments of the therapy system of FIG. 1.

FIG. 2 is a schematic top-view of an example of the dressing 102, illustrating additional details that may be associated with some embodiments. In some embodiments, a layer comprising or consisting essentially of a manifold 128 may be divided into a central region 140 and a perimeter region 141. The perimeter region 141 may contain a plurality of perforations 144 arranged in a pattern so as to define a plurality of sub-regions of the perimeter region. Some of the plurality of perforations 144, such as the innermost of perforations 144, may also serve as a dividing edge between the central region 140 and the perimeter region 141. The central region 140 is pictured as containing no perforations or fenestrations therethrough. Though the central region 140 of the manifold 128 may include perforations or fenestrations relating to provision of a negative-pressure source or provision of a fluid instillation source, typically a manifold need not have a plurality of perforations or fenestrations therethrough, particularly the central region 140 of the manifold 128 in FIG. 2. The perforations 144 in the perimeter region 141 of the manifold 128 may facilitate sizing or shaping of the manifold 128 and the dressing 102 in some embodiments, and may also serve a secondary function of assisting in provision or removal of fluid.

Figure 3:
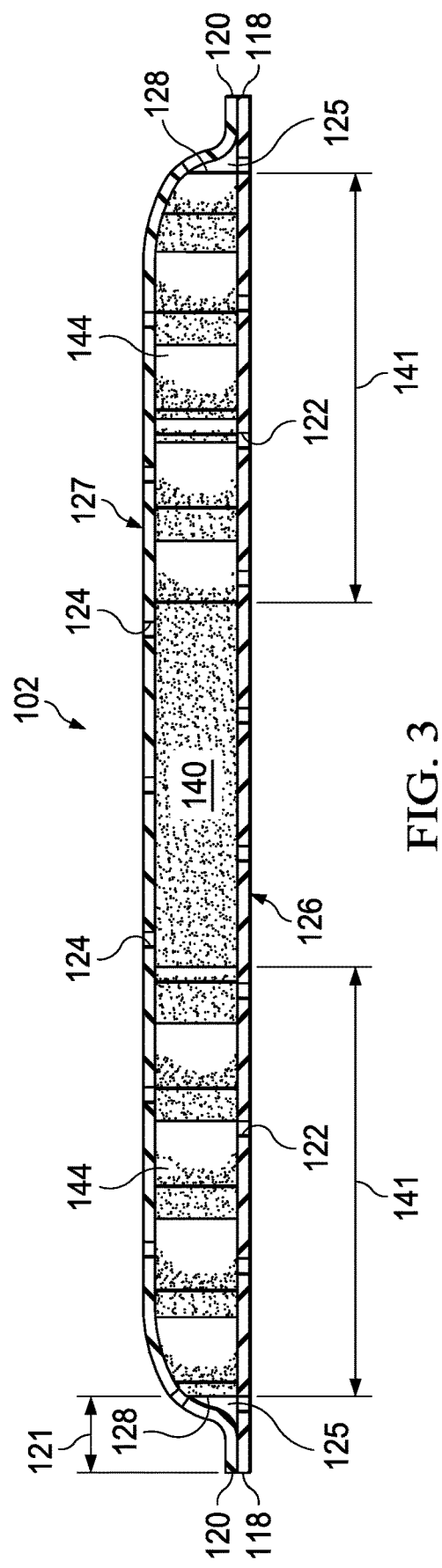
FIG. 3 is a schematic diagram, in cross-section, of the example embodiment of the dressing portion of FIG. 2.

FIG. 2 illustrates an example pattern of perforations 144 that may be associated with some embodiments of the dressing 102. In the example of FIG. 3, a plurality of the perforations 144 demarcate a division between the central region 140 of the manifold 128 and the perimeter region 141. The plurality of perforations 144 can also be seen to define a plurality of border sub-regions 146 within the perimeter region 141. In some embodiments, the perimeter region 141 may include a second plurality of perforations 147, as illustrated in the example of FIG. 2. In some embodiments, each of these additional perforations 147 contains a weld or bond therethrough, thereby coupling together a layer above the manifold 128 and a layer below the manifold 128. In some embodiments, a portion of the second plurality of perforations 147 may include perforations 148 containing captivating welds therethrough, which perforations 148 represent the innermost of the second plurality of perforations 147 within the perimeter region 141, closest to the central region 140. A further coupling of the layer above the manifold 128 and the layer below the manifold 128 in FIG. 2 is shown as a sealing portion 121 located near the outer edge of the manifold 128.

In some embodiments, the perimeter region 141 may be concentric with the central region 140. In some embodiments, the perimeter region 141 may have a central point, such as a center of mass, that is located within the central region 140. Whatever the relative shapes of inner and outer regions, a perimeter region surrounds an inner region in all directions outward, for example from a center point or from any point located within the inner region. In other words, there can be a 360-degree continuity between the central region 140 and the perimeter region 141. For example, FIG. 2 shows the manifold 128 to be an elliptical cylinder and the central region 140 to be a smaller central elliptical cylinder. In this example, the perimeter region 141, which is illustrated as an elliptical hollow cylinder, completely surrounds the central region 140 in the top-view of FIG. 2. While this example may seem to indicate a concentric symmetry with respect to the breadth of the perimeter region 141 of the manifold 128, that need not necessarily be the case, so long as the perimeter region 141 exhibits some portion completely surrounding the central region 140.

Welds or bonds through the perforations 147, through the perforations 148, or to the manifold 128, such as in the perimeter region 141, can function to hold the dressing 102 together, while still allowing the dressing 102 to be manually sized. In some embodiments, the central region 140 may be retained in place by captivating welds through perforations 148, and in some examples, captivating welds may define a boundary between the central region 140 and the perimeter region 141. In the case of welds through the perforations 147 and captivating welds through the perforations 148, the arrangement of the plurality of perforations 147 and perforations 148 throughout the perimeter region 141 may advantageously be dispersed to allow one or more border sub-regions 146 to be removed without significantly compromising the coupling of the tri-layer assembly. For example, in FIG. 2, perforations 147 and perforations 148 through which welds or bonds exist to couple the layers above and below the manifold 128 are arranged in each quadrant corresponding to the division of the perimeter region 141 into border sub-regions 146 by the perforations 144. By doing so, even excision of one or several of these welded-through perforations 147 along with a border sub-region 146 could allow the remaining welded-through perforations 147 and captivating weld perforations 148 to sufficiently anchor the layers above and below the manifold 128 through the remaining manifold 128. Although these weld points are exemplified in FIG. 2 to be as few as one weld-through perforation 147 or captivating weld perforation 148 per border sub-region 146, it should be understood that the pattern of welded-through perforations 147 and captivating weld perforations 148 in the perimeter region 141 could be any that provide adequate physical coupling of the tri-layer assembly. In addition, it should be reinforced that, though the plurality of perforations 144 may provide visual indicia for guiding an external user to more easily customize the manifold 128 or the dressing 102 to fit a given tissue site, the external user need not make use of that guide nor necessarily seek to make manual sizing easier.

FIG. 3 shows a cross-section of the dressing 102 of FIG. 2, as viewed along the line between the arrows labelled "3" at either end of FIG. 2. FIG. 3 illustrates the layer below the manifold 128 as a first liquid-impermeable layer 118 and the layer above the manifold 128 as a second liquid-impermeable layer 120, although the dressing 102 may be formed having a plurality of liquid-impermeable layers. The first liquid-impermeable layer 118 may be formed to have fenestrations 122, and the second liquid-impermeable layer 120 may be formed to have fenestrations 124. "Liquid-impermeable" with respect to "liquid-impermeable layers" means that the layers are formed with a liquid-impermeable material. Thus, although formed with a liquid-impermeable material, the layer may be liquid-permeable when fenestrated, but nonetheless is referred to as a liquid-impermeable layer.

The fenestrations 122 and 124 may take many shapes or combinations of shapes, including circular apertures, elliptical apertures, rectangular openings, or polygons, for example. The fenestrations 122 and 124 are presented in this illustrative embodiment as slits, or linear cuts.

In some embodiments, the first liquid-impermeable layer 118 and the second liquid-impermeable layer 120 may be sealingly coupled to one another along a sealing portion 121, as shown in FIG. 3. The coupling may be accomplished in any suitable manner, for example, without limitation, through chemical means or physical means or both, such as by welding, bonding, adhesives, cements, or other bonding mechanisms.

The first liquid-impermeable layer 118 may be adapted to be positioned between the second liquid-impermeable layer 120 and at least a portion of a tissue site. In the example embodiment of FIG. 3, a chamber 125 is formed between the first liquid-impermeable layer 118 and the second liquid-impermeable layer 120. The first liquid-impermeable layer 118 and the second liquid-impermeable layer 120 may each comprise or consist essentially of a non-adherent material, such as a medical drape, capable of inhibiting tissue from adhering to the non-adherent material. For example, in some embodiments, the first liquid-impermeable layer 118 and the second liquid-impermeable layer 120 may comprise a breathable polyurethane film.

As shown in FIG. 3, the chamber 125 between the first liquid-impermeable layer 118 and the second liquid-impermeable layer 120 can contain a third layer comprising or consisting essentially of the manifold 128.

In some embodiments, the manifold 128, or the third layer comprising the manifold 128, may be monolithic. In some embodiments, the manifold 128 does not comprise, and the chamber 125 does not contain, any manifolding elements extending outward from an outer edge of the perimeter region 141, for example radially. In some embodiments, the sealing portion 121 of the first liquid-impermeable layer 118 and second liquid-impermeable layer 120 may be releasably coupled together, for example using an adherent substance such as a low-tack or pressure-sensitive adhesive disposed therebetween. In some embodiments, a low-tack adhesive can also be applied between the manifold 128 and one or more of the first liquid-impermeable layer 118 and the second liquid-impermeable layer to further support the structural integrity of the dressing 102. The adhesive may also contain an antimicrobial compound in some examples. In some embodiments, the manifold 128 or the third layer comprising the manifold 128 may comprise an absorbent material adapted to absorb fluid and adapted to reduce, inhibit, or eliminate in vivo granulation. In one non-limiting example, the absorbent material may comprise a cross-linked hydrogel, such as a hydrophilic poly(vinyl alcohol), which can inhibit granulation in-growth and function as a fluid storage medium in some embodiments. The absorbent material may be present within or on one or more surfaces of the layer comprising manifolding member.

In some illustrative embodiments of operation of the therapy system 100, the dressing 102, or even the treatment device 101, may be sized to fit a given tissue site and disposed at or within the tissue site. For example, the dressing 102 may be sized to fit a compartment space such as an abdominal cavity. Excess portions of the dressing 102 or of the treatment device 101 may be removed to appropriately size the dressing 102 or the treatment device 101. In some embodiments, removal can occur by decoupling the sealing portion 121 of the first liquid-impermeable layer 118 and the second liquid-impermeable layer 120 and cutting or tearing the manifold 128 along some of the perforations 144 to remove one or more of the border sub-regions 146 of the perimeter region 141. In some embodiments, removal can occur by cutting or tearing the first liquid-impermeable layer 118, the second liquid-impermeable layer 120, and the manifold 128 altogether, optionally using some of the perforations 144 of the manifold 128 as a guide or optionally not using any visual indicia on the dressing 102.

In various embodiments, the surfaces of the dressing 102 may have any suitable shape, examples of which include, but are not limited to, triangles, squares, rhombuses, rhomboids, diamonds, rectangles, trapezoids, ellipses, ellipsoids, circles, semi-circles, pie-wedges, ovals, and various polygons having four, five, six, seven, eight, or more sides. These shapes may additionally or alternatively be adaptations of such common shapes. In some embodiments, shapes with typically rounded edges may be altered to be flatter, such as a rounded hexagonal/octagonal shape made by flattening the rounded edges of a circle. Additionally or alternatively, shapes with typically rounded edges may be altered to be sharper, such as a tear-drop shape made by sharpening a rounded end of an ellipse or ellipsoid, or such as an eye shape made by sharpening two rounded, opposing ends of an ellipse or ellipsoid. Further additionally or alternatively, shapes with typically pointed edges may be altered to be more rounded, such as for a blunt-ended triangle. Still further additionally or alternatively, shapes with typically flat edges may be altered to be more rounded, such as by converting the flat sides of any regular polygon to a sinusoidal edge exhibiting an undulating, curvy edge.

In some embodiments, the shapes of the surfaces of the dressing 102 may be limited, for example so as to ensure that no manifolding elements in the third layer comprising the manifold 128 extend outward from the outer edge of the perimeter region 141. In some embodiments, the shapes of the surfaces of the dressing 102, may be limited, for example such that the collective volume occupied by the plurality of fenestrations 144, the plurality of perforations 147, and the captivating weld perforations 148 are less than 50% of the volume of the perimeter region 141 of the manifold 128; in particular embodiments, the collective volume occupied by the plurality of fenestrations 144, the plurality of perforations 147, and the captivating weld perforations 148 are less than 35%, such as less than 25% or less than 20%, of the volume of the perimeter region 141 of the manifold 128. In some embodiments, none of the individual volumes of each fenestration 144, each perforation 147, and each perforation 148 exceed 5% of the volume of the perimeter region 141 of the manifold 128; in particular embodiments, none of the individual volumes of each fenestration 144, each perforation 147, and each perforation 148 exceed 3%, or 2%, of the volume of the perimeter region 141 of the manifold 128. In a particular embodiment, the perimeter region 141 of the manifold 128 is distinct from manifolding structures described in U.S. patent application Ser. No. 13/043,987, filed on Mar. 9, 2011, for example FIG. 2, as well as from any U.S. patent applications claiming priority thereto as a continuation or divisional application or claiming priority to U.S. Provisional Application No. 61/312,990, filed on Mar. 11, 2010, the contents of each of which are hereby incorporated by reference. In general, though, the size, shape, area, and volume of the surfaces of the dressing 102 may be customized to the location and type of tissue site which the therapy system 100 is to be used to treat.

Figure 4:
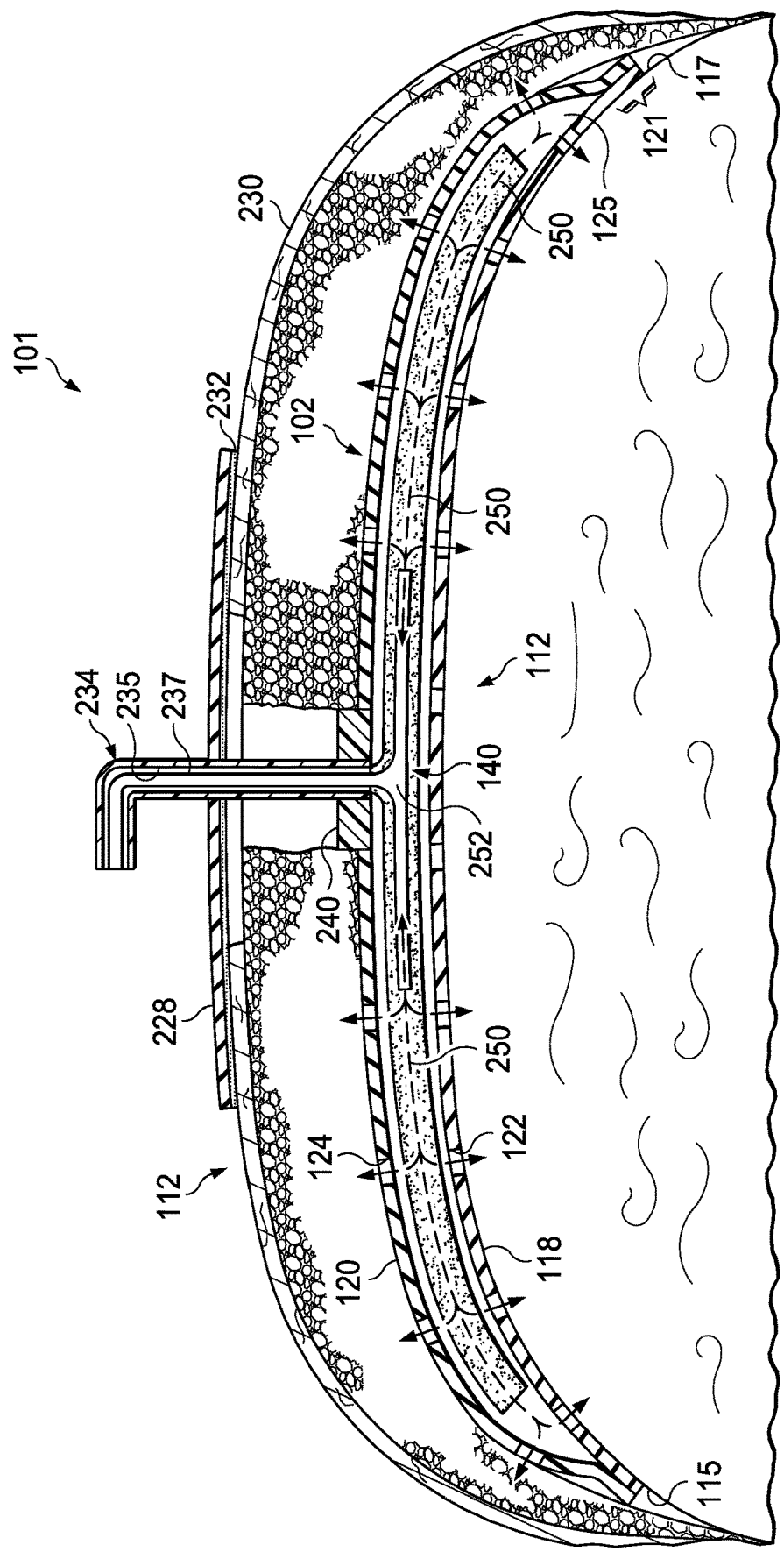
FIG. 4 is a schematic diagram, with a portion in cross-section, of an illustrative device for treating an abdominal cavity that may be associated with some embodiments of the therapy system of FIG. 1, with the dressing portion of FIGS. 2-3, or both.

FIG. 4 is a schematic diagram illustrating additional details that may be associated with some embodiments of the treatment device 101, for example incorporating the dressing 102 from FIGS. 2-3. The treatment device 101 of FIG. 4 is applied to a tissue site 112. In this illustrative embodiment, the tissue site 112 may include tissue in a body cavity, such as an abdominal cavity. The tissue site 112 may include abdominal contents or tissue that is proximate the abdominal cavity. Treatment of the tissue site 112 may include removal of fluids, e.g., ascites, protection of the abdominal cavity, or negative-pressure therapy.

As shown in FIG. 4, the dressing 102 may be disposed near or within a tissue site 112, which may be a compartmented site such as a peritoneal or an abdominal cavity, in order to treat the tissue site 112. In some abdominal cavities, for example, the dressing 102 may be supported by the abdominal contents, which can be generalized to most compartmented tissue sites. As depicted, a first portion of the dressing 102 may be positioned in or proximate to a first paracolic gutter 115, and a second portion of the dressing 102 may be placed in or proximate to a second paracolic gutter 117. The first paracolic gutter 115 and the second paracolic gutter 117 may each be, for example, an open space on opposing sides of the abdominal cavity among the abdominal contents. The first paracolic gutter 115 may be laterally disposed from the second paracolic gutter 117 or otherwise located on an opposite side of the tissue site 112 from the second paracolic gutter 117. Although FIG. 4 depicts the treatment device 101 deployed at an abdominal cavity, the treatment device 101 and therapy system 100 may be used at other types of tissue sites, particularly in which tissue contacts the treatment device 101, or more particularly the dressing 102, on both a first surface 126 and a second surface 127, shown in FIG. 3. Non-limiting examples of such tissue sites can include compartmented wounds, overhang wounds, tunnel wounds, flaps, or the like.

In some embodiments, the treatment device 101 may further include a cover 228 for providing a fluid seal over a tissue site 112, such as an abdominal cavity. In some embodiments, the cover 228 may generally be configured to provide a barrier to microbes, a barrier to external contamination, and protection from physical trauma. For example, the cover 228 may be constructed from a material that can reduce evaporative losses and provide a fluid seal between two components or two environments, such as between a therapeutic environment and a local external environment. The cover 228 may be formed from a suitable material, such as a polymer, for example, which may comprise or be an elastomeric film or membrane that can provide a seal at a tissue site. In examples involving application of negative pressure to a tissue site, the cover can provide a seal adequate to maintain negative pressure at a tissue site for a given negative-pressure source 106. In some embodiments, the cover 228 may comprise or be a polyurethane. In some embodiments, the cover 228 may have a high moisture-vapor transmission rate (MVTR). For example, in such an embodiment, the MVTR may be at least 300 g/m$^2$ per twenty-four hours. For example, the cover 228 may comprise a polymer drape, such as a polyurethane film, that may be permeable to water vapor but generally impermeable to liquid water. In some embodiments, the film or drape may have a thickness in the range of about from about 15 to about 50 microns. For permeable materials, the permeability generally should be low enough that a desired negative pressure may be maintained.

An attachment device, such as attachment device 232, may be used to attach the cover 228 to an attachment surface of a tissue site 112, such as the epidermis 230 of a patient. The attachment device 232 may be used to attach the cover 228 to a gasket, or another sealing member or cover. The attachment device 232 may take any of a variety of suitable forms. For example, an attachment device may be a medically-acceptable, pressure-sensitive adhesive that extends about a periphery, a portion, or an entire sealing member or cover. In some embodiments, for example, some or all of the cover 228 may be coated with an adherent layer, such as comprising an acrylic adhesive, having a coating weight between 25 and 65 grams per square meter (g.s.m.). Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organogel.

The illustrative systems and devices herein may optionally allow for the irrigation and washing out of a tissue site 112, for example a compartmented site such as a peritoneal or an abdominal cavity, with the controlled and regulated introduction of fluid. In some instances, it may be necessary to wash or cleanse a contaminated abdominal cavity, for example as a result of a perforated colon or sepsis. The therapy system 100 can provide means to instill fluid into an open abdomen to cleanse the abdominal contents, including reaching areas such as the small bowel loops, pancreas, etc. Additionally, the treatment device 101 and the therapy system 100 may provide temporary closure to an open abdomen, while optionally allowing for removal of fluid and reduction of edema. Thus, the therapy system 100 may provide the capability of performing washouts of a tissue site, such as a peritoneal or abdominal cavity, without having to repeatedly remove one or more dressings applied to the tissue site of a patient or bringing the patient into the operating room for manual fluid introduction procedures. The therapy system 100 may thus be able to provide a controlled and regulated full abdominal wash, for example via instillation of a therapeutic fluid, as well as have the capability to provide a targeted wash to certain areas within the abdomen when required. Some embodiments of the therapy system 100, and more particularly the dressing 102, may also provide support and maintenance of the fascial domain of an abdominal cavity, for example, and provide overall protection to the abdominal contents.

In some embodiments, the therapy system 100 may also include an interface for fluidly connecting the dressing 102 and other portions of the treatment device 101 to a conduit 234, as shown in FIG. 4. The interface may include a connector, which may comprise or be a part of a negative-pressure connector subsystem. Alternatively, the interface may be partially or fully embedded within a portion of the dressing 102, or configured in any other way possible for fluidly connecting the treatment device 101 to a therapy unit, such as the therapy unit 104 of FIG. 1. The conduit 234 may be fluidly coupled to negative-pressure source 106 and/or fluid source 108 of the therapy unit 104 for providing negative pressure and/or treatment fluid, respectively, to the treatment device 101. In some embodiments, the conduit 234 may include two substantially parallel, fluidly-isolated conduits, one of which for fluidly coupling the treatment device 101 to the negative-pressure source 106 and the other for fluidly coupling the treatment device 101 to the fluid source 108. Thus, in some embodiments, the conduit 234 may be a multi-lumen conduit with both a negative-pressure lumen 235 and a fluid withdrawal lumen 237. In some other illustrative embodiments, the conduit 234 may be replaced with two separate conduits, one containing a negative-pressure lumen and the other containing a fluid withdrawal lumen. In embodiments enabling fluid instillation, fluid withdrawal lumen 237 can be temporarily or intermittently repurposed to provide instillation fluid, instead of withdrawing fluid, in which situations fluid withdrawal lumen 237 can alternatively be referred to as a fluid supply lumen. In other embodiments enabling fluid instillation, the conduit 234 may be a multi-lumen conduit with a negative-pressure lumen 235, a fluid withdrawal lumen 237 in fluid communication with container 110, and a separate fluid supply lumen (not pictured in FIG. 4) in fluid communication with fluid source 108, which may be separate from container 110. In such multi-lumen embodiments, the negative-pressure, fluid withdrawal, and fluid supply lumens may be together within the same conduit 234 or may be in three separate conduits or in two separate conduits, for example with the fluid supply lumen in one conduit and the negative-pressure lumen 235 and the fluid withdrawal lumen 237 together in the other conduit.

In some embodiments, the therapy system 100 may further include a filler material 240, such as a portion of foam, disposed between the second liquid-impermeable layer 120 and the cover 228. The filler material 240 may be part of the interface and may be sized to fill the portion of abdominal volume beneath or surrounding an incision or opening into abdomen from the skin layers, such as a portion of abdominal cavity. In some embodiments, the filler material 240 may contain within it, or may itself serve as, a distribution manifold for negative pressure. For example, in some embodiments, the filler material 240 may be positioned between the second liquid-impermeable layer 120 and the cover 228, and a negative pressure lumen or conduit, such as negative-pressure lumen 235, may be pneumatically connected to the cover 228. As a result, fluid removal may occur from the layers of the treatment device 101 through the filler material 240 positioned atop second liquid-impermeable layer 120, and into the negative-pressure lumen 235. In some embodiments, the filler material may include a three-dimensional woven or non-woven fabric, such as TDL2 or TL4, commercially available from Libeltex of Meulebeke, Belgium, or 3DXD or 4DXD spacer fabrics, commercially available from Baltex of Derbyshire, England, or an open-cell, reticulated polyurethane foam such as GRANUFOAM™ Dressing or VERAFLOW™ Therapy foam, both available from KCI Licensing, Inc. of San Antonio, Tex.

Also not necessarily depicted in FIG. 4, a therapy method including fluid instillation can occur by periodically stopping application of negative pressure through the fluid withdrawal lumen 237 and initiating liquid supply through the same lumen, which can then alternatively be termed a fluid supply lumen. The negative-pressure lumen 235 may or may not experience an immediate halt in negative pressure application in such fluid instillation embodiments. In such embodiments, the manifold 128 can function both as fluid removal assembly and the optional fluid installation matrix, thereby enabling instillation fluid to be provided to the chamber 125, through the fenestrations 122 in the first liquid-impermeable layer 118 and through the fenestrations 124 in the second liquid-impermeable layer 120, and ultimately to the tissue site 112.

In some embodiments, the manifold 128 within the chamber 125 formed between the first liquid-impermeable layer 118 and the second liquid-impermeable layer 120 may function a fluid removal assembly for communicating negative pressure and removing fluids such as exudates from the tissue site 112, and optionally also an instillation matrix for delivering instillation fluid to the tissue site 112. As shown in FIG. 4, a plurality of fluid removal pathways 250 may extend inward through the fenestrations 122, through the fenestrations 124, through the manifold 128, and into fluid removal tubes positioned in the central region 140 of the manifold 128 and which are fluidly connected to the fluid withdrawal lumen 237.

In some embodiments, the plurality of fluid removal pathways 250 may be fluidly coupled to a fluid removal hub 252, which is optional but depicted in FIG. 4. The optional fluid removal hub 252 may serve as a distribution mechanism for communicating negative pressure to each of the fluid removal pathways 250 from the interface and the negative-pressure source 106. The fluid removal pathways 250 may take the form of numerous different shapes or be formed from a variety of materials. For example, in some embodiments, the fluid removal pathways 250 may be formed from portions of the first liquid-impermeable layer 118 and the second liquid-impermeable layer 120 that have been coupled together by a plurality of welds or bonds to form channels. Multi-lumen tubes may additionally or alternatively be a portion of the fluid removal pathways 250. Each of the different forms and configurations of fluid removal pathways 250 may also apply to fluid delivery tubes or to an instillation matrix, as applicable, especially in embodiments in which instillation fluid and negative pressure are not alternated using similar pathways but in reverse directions.

Figure 5:
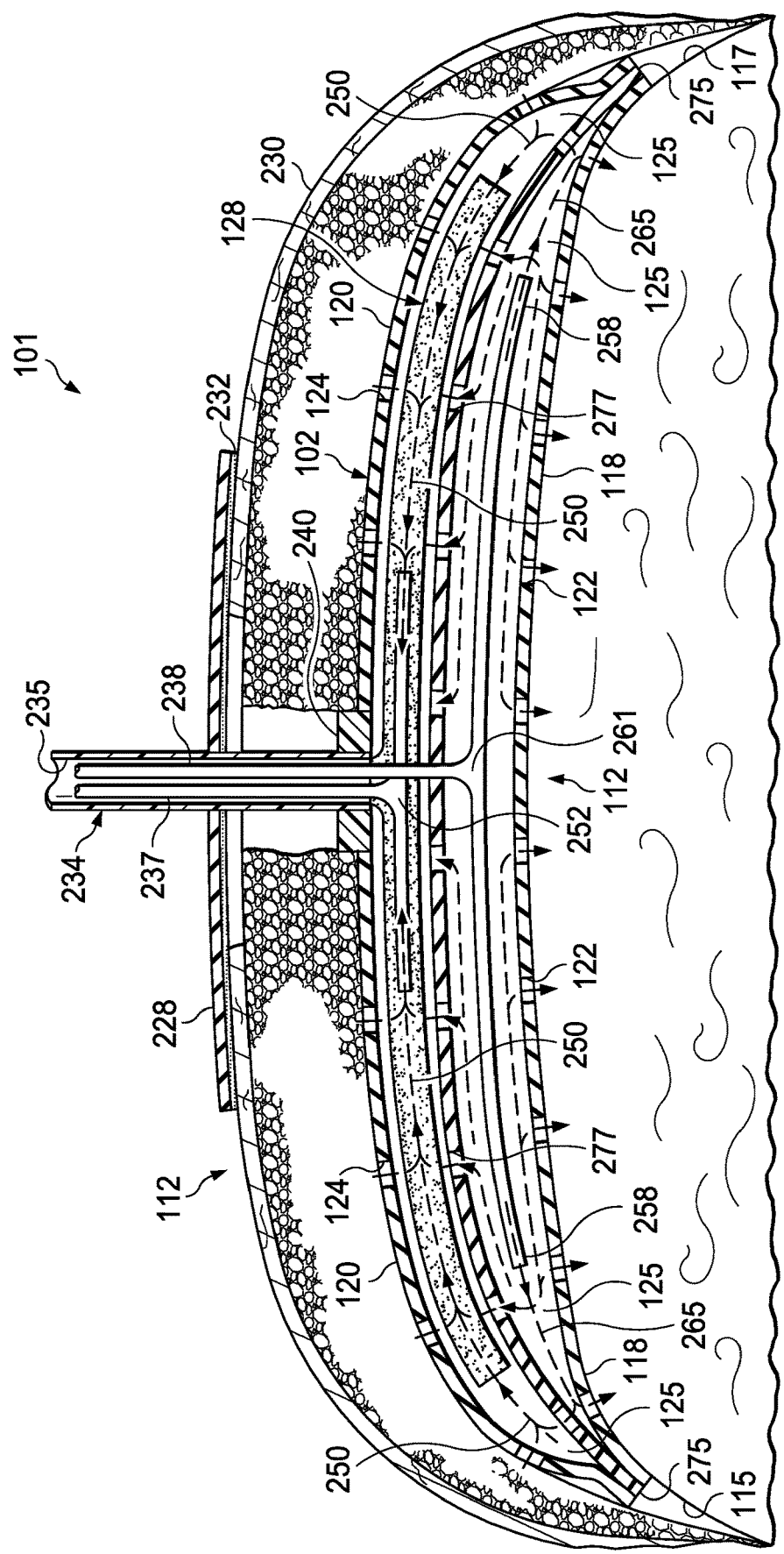
FIG. 5 is a schematic diagram, with a portion in cross-section, of an illustrative device for treating an abdominal cavity that may be associated with some embodiments of the therapy system of FIG. 1, with the dressing portion of FIGS. 2-3, or both.

Alternatively, as shown in FIG. 5, the optional fluid instillation system can be integral with but separate from the application of negative pressure for fluid collection. In some therapy embodiments, negative pressure can be applied at the same time as fluid is instilled, meaning that fluid withdrawal pathways and fluid supply pathways may need to be separated. For example, in FIG. 2, negative pressure can be applied to tissue site 112 by negative pressure source 106 through fluid removal pathways in the fluid removal assembly 148 in chamber 125 and through fluid withdrawal lumen 237 into container 110. Fluid or medicament can simultaneously be provided by fluid source 108 through fluid supply lumen 238 and through fluid supply pathways via a plurality of fluid delivery tubes 258 also in chamber 125. Although treatment device 101 may be adapted to simultaneously provide fluid or medicament with negative pressure, it is still contemplated that the therapy system 100 shown in FIG. 5 may be operated to alternate application of negative pressure and instillation of fluid, as desired.

In the example of FIG. 5, the fluid delivery tubes 258 and optional distribution hub 261 may be considered components of an instillation matrix and may be constructed of a variety of different materials, such as soft medical-grade silicone or PVC tubing material. The plurality of fluid delivery tubes 258 may vary in size, based on the particular size and application of the treatment device 101, as well as the conditions of the tissue site 112 to which the treatment device 101 is to be applied. For example, the fluid delivery tubes 258 may have an inner diameter of between 0.5 mm and 4 mm. In some embodiments, the fluid delivery tubes 258 may have an inner diameter of between 1 mm and 2 mm. The rather small size of the fluid delivery tubes 258 may be conducive for avoiding patient discomfort during therapy as well as ease of removal of the treatment device 101 following completion of therapy.

In some embodiments, the fluid removal tubes may additionally function to communicate negative pressure and draw fluids through both the ends as well as along the lengths of the fluid removal tubes. For example, some embodiments of the fluid removal tubes connected to fluid removal hub 252 may include open ends as well as openings or apertures, such as removal pathway apertures, along the length of the fluid removal tubes. In some embodiments, the fluid delivery tubes 258 may only have open ends, such as delivery ends, and may otherwise be fluidly isolated from the surroundings along the length of the fluid delivery tubes 258. In some embodiments, the treatment device 101 may be offered in a single size with the option to cut and remove portions of the treatment device 101 to reduce its size, thus potentially shortening the length of the fluid delivery tubes 258, as required on an individual patient basis. By having openings of the fluid delivery tubes 258 only at the ends of the individual tubes, greater levels of customization may be achieved since the fluid delivery tubes or instillation matrix do not rely on a set length of the fluid delivery tubes 258 or number or size of perforations along the fluid delivery tubes 258 to evenly distribute instillation fluid. In other embodiments, the fluid delivery tubes 258 may exhibit a plurality of perforations to enable more even distribution of instillation fluid across the chamber 125 and amongst the tissue site 112. In still other embodiments, rather than having open ends for delivering instillation fluid to a tissue site, each of the fluid delivery tubes 258 may instead have closed ends, such as delivery tube closed ends, and thus may include openings or perforations, such as delivery tube perforations. The fluid delivery tubes 258 may include both open ends as well as perforations along their lengths, should the particular need or application arise.

The fluid delivery tubes 258, as well as any other components of an instillation matrix, may be adapted to deliver fluids across the tissue site 112 in a substantially uniform manner. For example, each of the fluid delivery tubes 258, the delivery ends, and the delivery tube perforations may be adapted to provide substantially the same back-pressure. Such a configuration may prevent fluid from traveling more freely through or otherwise favoring one or more of the fluid delivery tubes 258 over another one or more of the fluid delivery tubes 258. Herein, back-pressure may refer to an increase in localized pressure caused by a resistance to fluid flow, such as through the confined space of a lumen or aperture. Back-pressure may result from the geometric configuration and material properties of the confined space, such as, without limitation, the size of the space, the presence and shape of bends or joints in the space, surface finishes within the space, and other characteristics. In some embodiments, a fluid hub, such as distribution hub 261, may not be necessary if the perforations along the lengths of the fluid delivery tubes 258 are sized to provide a substantially even distribution of fluid throughout the tissue site 112. Consistency among the size and configuration of the fluid delivery tubes 258, and the number and size of the delivery ends and delivery tube perforations in each of the fluid delivery tubes 258, for example, may enhance the uniformity of fluid delivery to the tissue site 112.

In some embodiments, the fluid delivery tubes 258 may have a cylindrical tube shape and may have an internal diameter between about 2 millimeters and about 6 millimeters. In some other embodiments, the fluid delivery tubes 258 may have an alternate tubing profile, where a lower-profile, or "flatter" tubing profile may be used to increase user comfort when the treatment device 101 is in place in a tissue site 112. The delivery apertures, in some embodiments, may have a diameter between about 0.1 millimeters and about 0.8 millimeters. Sizing the internal diameter or cross-section of the fluid delivery tubes 258 substantially larger than the size, cross-section, or diameter of the delivery ends and the delivery tube perforations may provide a substantially uniform pressure within each of the fluid delivery tubes 258. In such an embodiment, fluid flow velocity within the fluid delivery tubes 258 may be relatively low or substantially static in comparison to the relatively high fluid flow velocity through the delivery apertures.

Although not shown in the accompanying figures, in some embodiments, the fluid delivery tubes 258 may be arranged in the form of a grid, for example extending outward from a central hub 261, such as radially, with tubing segments that fluidly connect each of the outwardly-extending fluid delivery tubes 258. Perforations may exist along any or all portions of the outwardly-extending fluid delivery tubes 258, as well as the connecting tubing segments, in such embodiments.

In some embodiments, such as shown in FIG. 5, the treatment device 101 may comprise a distribution material for assisting with distributing the instillation fluid, such as filler material 240, as a complement to or an element of the distribution hub 261. Whether the distribution hub is elongate, cylindrical in shape, or bell-shaped, or comprises a fitting, such as a tube, tubular fitting, pipe, barbed connection, or similar structure, the distribution hub 261 or filler material 240 may generally be configured to be fluidly coupled between the fluid supply lumen 238 of the conduit 234 and the fluid delivery tubes 258.

Referring primarily to FIG. 5, the treatment device 101 may be adapted to provide negative pressure from the negative-pressure source 106 of the therapy unit 104 to a tissue site 112, such as an abdominal cavity, and to collect and transport fluid extracted from the tissue site 112. Additionally, the treatment device 101 may also be adapted to deliver a fluid, such as a treatment fluid or medicament, from the fluid source 108 of the therapy unit 104 to the tissue site 112. In some embodiments, the dressing 102 may include multiple liquid-impermeable layers, or visceral protective layers, which protect the underlying abdominal contents of the tissue site 112. For example, in some embodiments, the dressing 102 may include a first liquid-impermeable layer 118 having fenestrations 122 and a second liquid-impermeable layer 120 having fenestrations 124. In addition, in embodiments having simultaneous capability to provide negative pressure and fluid instillation, the dressing 102 may include a fourth liquid-impermeable layer 275. Though shown in FIG. 5 as containing fenestrations 122 and 124 for promoting fluid removal throughout an abdominal cavity, one or both of the first liquid-impermeable layer 118 and the second liquid-impermeable layer 120, respectively, may contain fenestrations only at the outer edges of the layer(s) or one of the layers may contain no fenestrations. Similarly, though shown in FIG. 5 as having a plurality of fenestrations 277, the fourth liquid-impermeable layer 275 may alternatively exhibit fenestrations only at the outer edges of the fourth liquid-impermeable layer 275 or no fenestrations at all, thereby partially or totally allowing for the instillation liquid to take a circuitous path out of the chamber 125 through fenestrations 122, among the abdominal contents, around the dressing 102, through fenestrations 124 back into the chamber 125, and through the fluid removal pathways 250 in the third layer comprising the manifold 128.

In some embodiments, such as shown in FIG. 5, the fourth liquid-impermeable layer 275 may be disposed within chamber 125 between the first liquid-impermeable layer 118 and the second liquid-impermeable layer 120, defining a first sub-chamber between the first liquid-impermeable layer 118 and the fourth liquid-impermeable layer 275 and a second sub-chamber between the second liquid-impermeable layer 120 and the fourth liquid-impermeable layer 275. In that circumstance, both sub-chambers are considered part of chamber 125. In alternative embodiments, the fourth liquid-impermeable layer may be disposed outside chamber 125, for example below first liquid-impermeable layer 118. In such an alternative example embodiment, the fourth liquid-impermeable layer 275 in FIG. 5 would be switched with the first liquid-impermeable layer 118, such that third layer comprising the manifold 128 and fluid removal pathways 250 would remain within chamber 125 but such that fluid delivery tubes 258 and optionally fluid instillation matrix (not shown) would be in a chamber outside chamber 125. In some embodiments, each of the liquid-impermeable layers may be formed from a polyurethane material, each having a thickness of between 25 μm and 500 μm.

Referring again to FIG. 5, the interface may provide both a negative-pressure connection as well as a fluid supply connection to the treatment device 101. The interface may be sized, shaped, or otherwise adapted to fluidly connect a negative-pressure lumen 235 and a fluid withdrawal lumen 237 of the conduit 234, as well as a separate fluid supply lumen 238 if desired, to the treatment device 101 in any suitable manner. In some embodiments, the interface may fluidly couple the negative-pressure lumen 235 and the fluid supply lumen 238 through the cover 228. For example, one or more sealing member apertures may be disposed through the cover 228 to provide fluid communication and access to the components of the treatment device 101 positioned within a sealed space involving the tissue site 112.

In some embodiments, the interface may be a multi-port interface providing both the negative-pressure connection and the fluid supply connection as individual, fluidly isolated ports within the multi-port interface, such as conduit 234. In such an embodiment, a wall of one of the individual lumens, such as the fluid withdrawal lumen 237 or the fluid supply lumen 238, may be coupled to the filler material 240 or to the distribution hub 261 for fluidly isolating the fluid supply connection from the negative-pressure connection.

Other configurations for maintaining the fluid isolation of the negative-pressure lumen 235 from the fluid supply lumen are possible.

FIG. 5 shows an exemplary embodiment in which fluid instillation pathways 265 emanating from distribution hub 261 through fluid instillation tubes 258 and are separate from fluid removal pathways 250 flowing into manifold 128 through fluid removal tubes and fluid removal hub 252. The configuration of providing the instillation fluid and the associated back-pressure along the fluid instillation pathways 265 through fluid instillation tubes 258 and using the distribution hub 261 may facilitate delivery of the instillation fluid to the tissue site 112 in a substantially uniform manner.

The treatment device 101 may be covered at the tissue site 112 with the cover 228 to provide a sealed space containing the treatment device 101. The cover 228 may be positioned and fluidly sealed about the tissue site 112 with the attachment device 232, as described above. Apertures in the cover 228 may be cut or otherwise disposed through the cover 228 as necessary, if not already provided as part of the cover 228. In some embodiments, instillation fluid may be independently fed from a fluid source, such as fluid source 108, through the fluid supply lumen 238 and into the chamber 125. Thus, in some embodiments such as shown in FIG. 5, the instillation fluid may be fed directly to a fluid hub, such as distribution hub 261, and therefore, the fluid instillation pathways 265 and the fluid removal pathways 250 may be controlled as separate entities. In these embodiments, potential contamination of clean fluid instillation pathways may be reduced or largely eliminated, and a more efficient cleansing cycle may be obtained. In other embodiments such as shown in FIG. 4, the instillation fluid may also be fed directly into a fluid hub and through fluid distribution pathways, but a single hub and a single set of pathways would function for both fluid instillation and fluid removal. In those embodiments, fluid removal hub 252 in FIG. 4 would function to assist fluid removal under negative-pressure conditions and to assist fluid instillation under conditions for flowing fluid to tissue site 112; similarly, fluid removal pathways 250 in FIG. 4 wound function in the arrow directions to assist fluid removal under negative-pressure conditions and opposite from the arrow directions to assist fluid instillation under conditions for flowing fluid to tissue site 112. Depending on how the components of the treatment device 101 are specifically configured, in some embodiments such as shown in FIG. 5, fluid may be fed through the fluid instillation tubes 258 directly into low points of an abdomen, such as the paracolic gutters 115,117.

Activating the negative-pressure source 106 may provide negative pressure to the negative-pressure lumen 235 of the conduit 234 and to the manifold 128 through the fluid withdrawal lumen 237. The fluid source 108 may provide instillation fluid to the chamber 125 through the fluid supply lumen 238 (or through repurposed fluid removal lumen 237, such as in FIG. 4), for example, by activing a pump or positive-pressure source in the fluid source 108, or by operation of gravitational or manual user forces acting on the instillation fluid. Negative pressure and instillation fluid may be provided to the treatment device 101 simultaneously, or cyclically, at alternate times. Further, negative pressure and instillation fluid may be applied to the treatment device 101 intermittently or continuously.

When the negative-pressure source 106 is activated, the fluid removal lumen 237 of the conduit 234 may distribute the negative pressure to the manifold 128 or optionally to the fluid removal hub 252 in fluid communication therewith. Fluid from the tissue site 112 may be drawn or extracted through the open ends and removal pathway apertures into the fluid removal pathways 250. Fluid may be moved through the fluid removal pathways 250 and optionally into fluid removal hub 252, where the fluid may be drawn into the fluid withdrawal lumen 237 of the conduit 234 and ultimately the container 110.

In some embodiments, some portion of fluid extracted from the tissue site 112 may be stored within the manifold 128 of the treatment device 101 before being drawn into the fluid withdrawal lumen 237. The capability to provide fluid storage and permeability while under negative pressure may require the manifold 128 or other porous portion of the third layer disposed between the first liquid-impermeable layer 118 and the second liquid-impermeable layer 120 to have a higher volume of fluid capacity compared to that of the fluid delivery tubes 258 that may be under positive pressure. Fluid being instilled or delivered to the tissue site 112, for example through fluid delivery tubes 258, may not be required to first pass through portions of the treatment device 101, such as the manifold 128, that may encompass a larger volume. Such a configuration is shown in FIG. 5 and may enhance the distribution and efficient use of the instillation fluid. Following completion of negative-pressure and/or fluid instillation therapy, a user may remove the treatment device 101 as a largely intact structure, thus maintaining an ease of use of the treatment device 101.

In some embodiments, the fluid delivery tubes 258 may comprise polyurethane film or foam bags with perforations. For example, the fluid delivery tubes 258 may be constructed using two layers of polyurethane film of approximately 100 micrometers in thickness that are edge-welded together. The fluid delivery tubes 258 may have open ends for targeted fluid delivery. In some embodiments, within each of the fluid delivery tubes 258 and the optional fluid removal hub 252 may be a central core adapted to ensure that an open pathway is maintained and to aid a user with handling during placement. For example, this central core may be an open-cell foam, such as a reticulated polyurethane. Dimensions of the central core material positioned within the fluid delivery tubes 258 may vary; for example, the central core material may range from around 2 mm to 10 mm in thickness by about 5 mm to 15 mm in width. In some embodiments, the central core material may be around 6 mm in thickness by 10 mm in width. The length of the central core material may be varied based on overall sizing considerations of the treatment device 101. Some embodiments may include a central core material having a width that varies along its length, which may allow for break points to provide user customization and sizing. In some instances, the fluid delivery tubes 258 may be adapted so that any instillation fluid remaining within the fluid delivery tubes 258 following delivery of instillation fluid by the fluid source 108 may be squeezed from the fluid delivery tubes 258 when negative pressure is applied to the treatment device 101, thus ensuring that substantially all instillation fluid is emptied from the fluid delivery tubes 258 to better regulate the volume of instillation fluid provided during therapy cycles.

In some embodiments, fluid instillation may optionally incorporate a layer of manifolding material or matrix, which may be referred to as an optional instillation matrix. In FIG. 4, the manifold 128 may serve that purpose, when not being used for fluid removal. In FIG. 5, the optional instillation matrix could surround the fluid delivery tubes 258 and be oriented between the fourth liquid-impermeable layer 275 and the first liquid-impermeable layer 118. If present, the optional installation matrix could help ensure that the fluid instillation pathway remains open and not occluded or sealed when subjected to negative pressure. Example materials for the optional instillation matrix may be similar to those for the manifold 128 and may include foams, such as polyurethane foam, Libeltex TDL2, Libeltex TL4, Baltex 3DXD spacer fabrics, Baltex 4DXD spacer fabrics, embossed films, or some other formed structure.

In some additional methods for providing negative-pressure therapy and fluid instillation to a tissue site, rather than an automated or other form of mechanical instillation device, a manually-controlled instillation vessel, such as a fluid bag, bottle, or other vessel, may be incorporated. Thus, in some embodiments, during a first stage of a therapy cycle, a negative-pressure source may apply negative-pressure therapy to a treatment device and tissue site, while a device such as a clamp, valve, or other form of closure device may prevent fluid from being communicated from the manually-controlled instillation vessel to the treatment device and tissue site. In some embodiments, during a subsequent stage of a therapy cycle, a user may open the clamp or other form of closure device and may manually regulate the volume of fluid being instilled. During this instillation phase, the negative-pressure source may remain active, thus providing immediate removal of the instilled fluid from the treatment device and tissue site. Thus, there may be virtually no dwell time of the fluid in the tissue site, according to some embodiments of the method. The user may then re-clamp or otherwise close the closure device, thus stopping the flow of instillation fluid from the manually-controlled instillation vessel. The negative-pressure source may then continue to remove excess or remaining instillation fluid, as well as exudates, from the treatment device and tissue site. In some other embodiments of the disclosed method, rather than allowing the negative-pressure source to remain active while the fluid is instilled from the manually-controlled instillation vessel, the negative-pressure source may be paused, thus allowing the instillation fluid to dwell in the tissue site for a prescribed period of time. When appropriate, the user may close off the manually-controlled instillation vessel from delivering instillation fluid. Prior or subsequent to instillation being stopped, negative-pressure therapy may be recommenced, during which time any excess or remaining fluids may be removed from the treatment device and tissue site. In some embodiments, the negative-pressure source may remain active, while instillation fluid may be periodically provided in various stages.

The systems, apparatuses, and methods described herein may provide significant advantages. For example, some embodiments of the treatment device 101 may provide a combined temporary abdominal closure dressing system with fluid instillation capability through an independent matrix of fluid delivery tubing, as well as negative-pressure fluid removal pathways for removal of contaminated fluid. Some embodiments may provide means for irrigating and cleansing an abdominal cavity while supporting and protecting the abdominal contents, as well as removing contaminated fluid and controlling and/or reducing edema. Additionally, as a result of the various layers and components of the dressing 102 applying tension and closing force to the abdominal contents, quicker primary fascia closure of the abdominal cavity may be facilitated.

In some embodiments, the therapy system 100 may provide means for irrigating all areas of an abdominal cavity, including small bowel loops, gutters, retroperitoneal space, portions of the lymphatic system, etc., all while the dressing system is in place, advantageously reducing time required for patients and clinical staff in the operating room. Various embodiments can offer configurations of fluid pathways designed to maximize the exposure of internal organs of abdominal tissue sites to fluid instillation therapy. Other embodiments of instillation are additionally or alternatively possible, particularly in combination with the embodiments herein in which neither the fluid removal assembly layer containing a manifolding material nor the chamber in which it is disposed contain any manifolding elements extending outward from an outer edge of the perimeter region—some non-limiting examples of instillation arrangements that may be useful include those disclosed in U.S. Provisional Application No. 62/451,284, filed on Jan. 27, 2017, the contents of which are hereby incorporated by reference. Some embodiments may also allow for longer dressing application times without adhering to the fascia of abdominal tissue sites. In some embodiments, repeatable as well as reliable fluid instillation that may be provided relatively evenly to various portions of a tissue site. In some embodiments, fluid irrigation and cleansing may be relatively consistent, advantageously leading to a reduction in mortality of patients suffering from septic abdominal cavities. Fluid instillation may be managed at a patient's bedside and may be custom-tailored and adjusted on a case-by-case basis.

Use of the therapy system 100 may enable exudate and infectious material to be drained from tissue sites, such as the abdominal cavity, which can reduce the presence of contaminated abdominal fluids to promote healing. Furthermore, the therapy system 100 may provide separate instillation and negative-pressure pathways to ensure that contaminated fluid is fully removed from the tissue site 112. In some embodiments of the therapy system 100, instillation fluid may not be recirculated back into the tissue site, which can increase the clinical benefits of irrigating tissue sites.

The design of the therapy system 100 or specific portions thereof may also allow for user sizing and/or customization at the time of application to a patient in the operating room. In some embodiments, improved ease of use for dressing placement, sizing, and removal may be provided by built-in sizing or placement visual markings or indicators for guiding users. Some embodiments of the disclosed dressing systems may also include various components, such as the fluid instillation pathways and/or fluid removal pathways already pre-attached to the structural dressing layers to further streamline and simplify use. In some embodiments, not only may improved fluid delivery and removal be enabled, as compared to existing dressing systems, but increased ease of use may be promoted.

In some embodiments, the therapy system 100, and particularly one or more layers or portions of the dressing 102, may optionally comprise one or more additional materials. Such optional components may include, for example, active materials such as preservatives, stabilizing agents, plasticizers, matrix strengthening materials, dyestuffs, and combinations thereof.

Additionally or alternatively, the therapy system 100, and particularly one or more layers or portions of the dressing 102, may comprise one or more additional active materials, for example, antimicrobial agents that may be effective to aid in wound healing. Non-limiting examples of such active materials may include non-steroidal anti-inflammatory drugs such as acetaminophen, steroids, antimicrobial agents such as penicillins or streptomycins, antiseptics such as chlorhexidine, growth factors such as fibroblast growth factor or platelet derived growth factor, and other well-known therapeutic agents, alone or in combination. If present, such active materials may typically be included at any effective level that show therapeutic efficacy, while preferably not being at such a high level as to significantly counteract any critical or desired physical, chemical, or biological property of the wound dressing. Depending upon the therapeutic goal(s), the active material(s) may be loaded at a level of from about 10 wppm to about 10 wt % of the layer(s) in which it(they) are present, for example, from about 50 wppm to about 5 wt % or from about 100 wppm to about 1 wt %.

In some embodiments, the antimicrobial agents may comprise a safe and effective amount of poly(hexamethylene biguanide) ("PHMB"), which is also known as polyaminopropyl biguanid ("PAPB") and polyhexanide, having the following general formula.

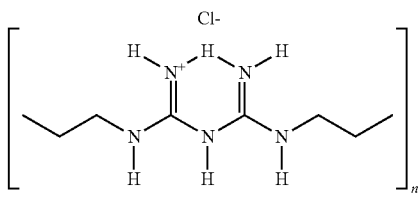

PHMB can be a cationic broad spectrum antimicrobial agent. PHMB may be synthesized by a variety of methods, including polycondensation of sodium dicyanamide and hexamethylenediamine. PHMB is commercially available from a variety of sources. In some embodiments, the PHMB may be present in one or more of the dressing layers at a level of from about 0.005 wt % to about 0.025 wt % of each layer in which it is present, particularly from about 0.007 wt % to about 0.2 wt % or from about 0.008 wt % to about 0.012 wt %, or in some cases at about 0.01 wt %. In some embodiments, the PHMB may be present in one or more of the dressing layers at a level of from about 0.05 wt % to about 3 wt % of each layer in which it is present, particularly from about 0.1 wt % to about 2.5 wt %, from about 0.3 wt % to about 2 wt %, from about 0.5 wt % to about 1.5 wt %, or in some cases at about 1 wt %. In alternative embodiments, silver compounds having antimicrobial efficacy may completely or partially replace the PHMB, as desired. In alternative embodiments, silver compounds having antimicrobial efficacy may completely or partially replace the PHMB, as desired.

Additionally or alternatively, the claimed subject matter may include one or more of the following embodiments.

Embodiment 1. A dressing for treating a tissue site, the dressing comprising: a first layer being made from a liquid-impermeable material and being at least partially fenestrated; a second layer being made from a liquid-impermeable material and being at least partially fenestrated, the second layer coupled to the first layer to define a chamber between the first layer and the second layer; and a third layer disposed within the chamber, the third layer comprising a manifold having a central region and a perimeter region, the perimeter region containing perforations arranged in a pattern that defines a plurality of sub-regions of the perimeter region, wherein the first layer and the second layer are coupled together by a plurality of welds or bonds through the perimeter region of the third layer comprising the manifold.

Embodiment 2. The dressing of embodiment 1, wherein the chamber further comprises a plurality of fluid removal pathways, substantially all of which flow through the manifold.

Embodiment 3. The dressing of embodiment 1 or embodiment 2, wherein the manifold is monolithic and wherein the plurality of welds or bends extends through at least some of the perforations in the perimeter region.

Embodiment 4. The dressing of any of embodiments 1-3, wherein each of the plurality of sub-regions from the perimeter region is configured to be manually removable by a user.

Embodiment 5. The dressing of any of embodiments 1-4, wherein the first layer and the second layer are releasably coupled together near their outer edges.

Embodiment 6. The dressing of any of embodiments 1-5, wherein the first layer and the second layer are coupled together by a plurality of bonds to the perimeter region of the third layer comprising the manifold.

Embodiment 7. The dressing of embodiment 6, the coupling further comprising a low-tack adhesive bonding the first layer to the second layer.

Embodiment 8. The dressing of any of embodiments 1-7, wherein the third layer does not comprise, and the chamber does not contain, any manifolding leg elements extending outward from an outer edge of the perimeter region.

Embodiment 9. The dressing of any of embodiments 1-8, wherein the chamber comprises an effective amount of one or more of an antiseptic and an antimicrobial agent.

Embodiment 10. The dressing of any of embodiments 1-9, wherein the third layer further comprises an absorbent material, such as a cross-linked hydrogel, adapted to reduce, inhibit, or eliminate granulation in vivo and adapted to absorb fluid.

Embodiment 11. The dressing of any of embodiments 1-10, wherein the first layer and the second layer each comprise a polyurethane film, wherein the first layer and the second layer each have a thickness of between 25 µm and 500 µm, or both.

Embodiment 12. The dressing of any one of embodiments 1-11, further comprising: a filler member disposed above the central region of the manifold; and a cover disposed above the filler member and configured to form a seal with a tissue site.

Embodiment 13. The dressing of embodiment 12, wherein the cover comprises a polyurethane drape and an adherent layer adapted to sealably couple the polyurethane drape to the tissue site.

Embodiment 14. A dressing for treating a tissue site, the dressing comprising: a first layer being made from a liquid-impermeable material and being at least partially fenestrated; a second layer being made from a liquid-impermeable material and being at least partially fenestrated, the second layer coupled to the first layer to define a chamber between the first layer and the second layer; and a third layer disposed within the chamber, the third layer comprising a manifold having a central region and a perimeter region, the perimeter region containing perforations arranged in a pattern that defines a plurality of sub-regions of the perimeter region, wherein the manifold does not comprise, and the chamber does not contain, any manifolding elements extending outward from an outer edge of the perimeter region, and wherein the first layer and the second layer are coupled together by a plurality of welds or bonds through the perimeter region of the third layer comprising the manifold.

Embodiment 15. A system for treating a tissue site with negative pressure, the system comprising: a dressing according to any of embodiments 1-14; and a negative-pressure source fluidly coupled to a plurality of fluid removal pathways via the manifold layer.

Embodiment 16. The system of embodiment 15, further comprising: a negative-pressure conduit; a negative-pressure connector subsystem for fluidly coupling the negative-pressure source to the plurality of fluid removal pathways via the manifold layer; and optionally a container fluidly coupled to the negative-pressure source and the dressing and adapted to collect fluid.

Embodiment 17. The system of any of embodiments 15-16, further comprising: a fluid source coupled to and in fluid communication with the dressing; and a plurality of fluid delivery pathways formed within the chamber and configured to be in fluid communication with the fluid source, wherein the fluid delivery pathways are also in fluid communication with the fluid removal pathways via the manifold.

Embodiment 18. The system of embodiment 17, wherein the plurality of fluid delivery pathways comprise openings at peripheral ends or perforations along a length of each fluid delivery pathway, are disposed between the third layer and the first layer, or both.

Embodiment 19. The system of embodiment 18, wherein the plurality of fluid delivery pathways are disposed on the first layer outside, but in fluid communication with, the chamber.

Embodiment 20. The system of embodiment 18 or embodiment 19, further comprising a fourth layer being made of a liquid-impermeable material and coupled to the first layer to provide a fluid delivery space, wherein the perforations along the length of the fluid delivery pathways are formed by apertures in the fourth layer or by apertures or fenestrations in the first layer.

Embodiment 21. The system of any of embodiments 17-20, further comprising a centrally-positioned hub in fluid communication with the plurality of fluid delivery pathways.

Embodiment 22. The system of any of embodiments 17-21, further comprising a central manifold configured for fluid delivery and configured to be a part of the plurality of fluid removal pathways, which central manifold is within the filler member when the filler member is present.

Embodiment 23. The system of embodiment 22, wherein the filler member comprises a polyurethane foam or a three-dimensional textile form.

Embodiment 24. The system of any of embodiments 15-23, further comprising a sensor configured to sense relative changes in one or more variables, including pressure, temperature, pH, relative humidity, and location, near the tissue site.

Embodiment 25. The system of embodiment 24, wherein the sensor is configured to wirelessly provide information regarding the one or more variables to a person or to a pressure control system configured to control the negative-pressure source.

Embodiment 26. A method for treating a compartmented wound site, such as a peritoneal or abdominal cavity, the method comprising: opening the compartmented wound site to form an open cavity; deploying within the compartmented wound site the dressing of any of embodiments 1-14 or at least a portion of the system for treating a tissue site according to any of embodiments 15-25; deploying a negative-pressure connector subsystem; deploying a cover to form a fluid seal over the open cavity; fluidly coupling the negative-pressure connector subsystem to a negative-pressure source; and activating the negative-pressure source.

While shown in a few illustrative embodiments, a person having ordinary skill in the art will recognize that the systems, apparatuses, and methods described herein are susceptible to various changes and modifications. Moreover, descriptions of various alternatives using terms such as "or" do not require mutual exclusivity unless clearly required by the context, and the indefinite articles "a" or "an" do not limit the subject to a single instance unless clearly required by the context. Further, any feature described in connection with any one embodiment may also be applicable to any other embodiment. Components may be also be combined or eliminated in various configurations for purposes of sale, manufacture, assembly, or use. For example, in some configurations the treatment device 101 including the dressing 102, the container 110, or both may be eliminated or separated from other components for manufacture or sale. In other example configurations, the controller 109 may additionally or alternatively be manufactured, configured, assembled, or sold independently of other components.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described herein may also be combined or replaced by alternative features serving the same, equivalent, or similar purpose without departing from the scope of the invention defined by the appended claims.

What is claimed is:

1. A dressing for treating a tissue site, the dressing comprising:
   a first layer being made from a liquid-impermeable material and being at least partially fenestrated;
   a second layer being made from a liquid-impermeable material and being at least partially fenestrated, the second layer coupled to the first layer to define a chamber between the first layer and the second layer; and
   a third layer disposed within the chamber, the third layer comprising a manifold having a central region and a perimeter region, the perimeter region containing a plurality of first perforations and at least one second perforation, at least a portion of the first perforations surrounding at least one sub-region and the at least one second perforation;
   wherein the first layer and the second layer are coupled together by a weld or bond positioned through the at least one second perforation in the third layer;
   wherein the first layer and the second layer are not coupled through the plurality of first perforations;
   wherein the first layer and the second layer are releasably coupled together near their outer edges.

2. The dressing of claim 1, wherein the chamber further comprises a plurality of fluid removal pathways fluidly coupled with the manifold.

3. The dressing of claim 1, further comprising a second sub-region and another of the second perforations surrounded by another portion of the plurality of first perforations, wherein the first layer and the second layer are coupled together by another weld or bond positioned through the another of the second perforations.

4. The dressing of claim 1, wherein the at least one sub-region is configured to be manually removable by a user.

5. The dressing of claim 1, the coupling further comprising a low-tack adhesive bonding the first layer to the second layer.

6. The dressing of claim 1, wherein the manifold of the third layer does not extend radially outward from an outer edge of the perimeter region.

7. The dressing of claim 1, wherein the chamber comprises one or more of an antiseptic and an antimicrobial agent.

8. The dressing of claim 1, wherein the third layer further comprises an absorbent material adapted to reduce, inhibit, or eliminate granulation in vivo and adapted to absorb fluid.

9. The dressing of claim 8, wherein the absorbent material comprises a cross-linked hydrogel.

10. The dressing of claim 1, wherein the first layer and the second layer each comprises a polyurethane film.

11. The dressing of claim 10, wherein the first layer and the second layer each has a thickness of between 25 μm and 500 μm.

12. The dressing of claim 1, further comprising:
a filler member disposed above the central region of the manifold; and
a cover disposed above the filler member and configured to form a seal with a tissue site.

13. The dressing of claim 12, wherein the cover comprises a polyurethane drape and an adherent layer adapted to sealably couple the polyurethane drape to the tissue site.

14. A dressing for treating a tissue site, the dressing comprising:
a first layer being made from a liquid-impermeable material and being at least partially fenestrated;
a second layer being made from a liquid-impermeable material and being at least partially fenestrated; and
a third layer comprising a manifold positioned between the first layer and the second layer, the third layer including a first plurality of perforations and at least one second perforation, at least a portion of the first plurality of perforations surrounding at least one removable portion of the manifold;
wherein the first layer and the second layer are coupled together through the at least one second perforation, and wherein the first layer and the second layer are not coupled through the first plurality of perforations.

* * * * *